US007491703B2

United States Patent
Khavinson et al.

(10) Patent No.: US 7,491,703 B2
(45) Date of Patent: Feb. 17, 2009

(54) TETRAPEPTIDE REGULATING BLOOD GLUCOSE LEVEL IN DIABETES MELLITUS

(75) Inventors: Vladimir Khatskelevich Khavinson, St. Petersburg (RU); Vladimir Viktorovich Malinin, St. Petersburg (RU); Evgeny Iosifovich Grigoriev, St. Petersburg (RU); Galina Anatolievna Ryzhak, St. Petersburg (RU)

(73) Assignee: "Access Bioscience" CJSC, St. Petersburg (RU)

( * ) Notice: Subject to any disclaimer, the term of this patent is extended or adjusted under 35 U.S.C. 154(b) by 238 days.

(21) Appl. No.: 10/580,957

(22) PCT Filed: Aug. 9, 2004

(86) PCT No.: PCT/RU2004/000318

§ 371 (c)(1),
(2), (4) Date: May 30, 2006

(87) PCT Pub. No.: WO2005/056580

PCT Pub. Date: Jun. 23, 2005

(65) Prior Publication Data

US 2007/0142298 A1    Jun. 21, 2007

(30) Foreign Application Priority Data

Dec. 10, 2003    (RU)    ............................... 2003135605

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. ........................................ 514/18; 530/330
(58) Field of Classification Search ........................ None
See application file for complete search history.

(56) References Cited

U.S. PATENT DOCUMENTS

| 6,180,103 B1 | 1/2001 | Cohen et al. | |
| 7,101,854 B2 * | 9/2006 | Khavinson | ................... 514/18 |
| 2004/0054130 A1 | 3/2004 | Ng et al. | |

FOREIGN PATENT DOCUMENTS

| RU | 2078769 C1 | 5/1997 |
| WO | WO 01/72770 A1 | 10/2001 |

OTHER PUBLICATIONS

Schatz et al. Why Can't We Prevent Type 1 Diabetes. Diabetes Care, Dec. 2003. vol. 26, No. 12, pp. 3326-3328.*
National Diabetes Fact Sheet. http://www.cdc.gov/diabetes/pubs/general.htm accessed online Apr. 7, 2008; pp. 1-4.*
Ng, FM et al., *The minimal amino acid sequence of the insulin-potentiating fragments of human growth hormone: its mechanism of action*, Diabetes, vol. 29 Issue 10, pp. 782-787, 1980. (Abstract Only).
Balabolkin, M.I., *Diabetology*, Mockba 2000 pp. 572-583.
*Register of Pharmaceutical Substances*, Acarbose pp. 58-59, Glipizide pp. 236-237, Metformin pp. 517-518, Siofor p. 759.

* cited by examiner

*Primary Examiner*—Cecilia Tsang
*Assistant Examiner*—Marcela M Cordero Garcia
(74) *Attorney, Agent, or Firm*—Leydig, Voit & Mayer, Ltd.

(57) ABSTRACT

The invention refers to the field of medicine and can be applied as a substance capable of regulating glucose level while treating and preventing diabetes mellitus. There is proposed a biologically active new tetrapeptide lysyl-glutamyl-aspartyl-tryp-tophane of general formula Lys-Glu-Asp-Trp-$NH_2$ capable of regulating the glucose level, and pharmacological substance containing an effective amount of tetrapeptide lysyl-glutamyl-aspartyl-tryptophane of the general formula Lys-Glu-Asp-Trp-$NH_2$. There is proposed the method of prevention and/or treatment of the diabetes mellitus, which consists in administering to a patient of the pharmacological substance, containing as an active peptide agent an effective amount of Lys-Glu-Asp-Trp-$NH_2$ tetrapeptide in doses of 0.1-30 µg/kg of the body weight at least once a day for a period necessary for attaining a therapeutic effect.

8 Claims, No Drawings

TETRAPEPTIDE REGULATING BLOOD GLUCOSE LEVEL IN DIABETES MELLITUS

The invention refers to the field of medicine and may be applied for the diabetes mellitus treatment as a substance regulating glucose concentration.

Among the closest indication analogues of this substance, there are known insulin preparations, used for type 1 diabetes mellitus treatment. The choice preparation is a recombinant or genetically modified short acting human insulin preparation: Actrapid, Humulin R, Insuman R, Biosulin R, and human insulin preparations of the prolonged effect: Protophane, Humulin N, Insuman-Basal and Biosulin N—human insulin analogues of the short-term and prolonged effect. Preparations Humalog and Novorapid, are the preparations of ultra-short effect group, they are notable for the quick onset effect and a little bit short period of peak effect compared to the insulins of the short effect; they are effective in diminishing decrease of postprandial glucose level. Nevertheless insulin therapy is a replacing therapy, which can lead to some complications, such as allergic reactions, hypoglycemic states, insulin resistance and post-insulin lipo-dystrophy. The type 2 diabetes mellitus medical therapy has also changed due to the introduction into the clinical practice of short-term effect preparations, such as Novonorm or Repaglinid and Starlix. There are traditionally used sulphonylureas, such as: Glibenclamide group, Glipizide, Gliklazide group, Glikvidon and Arnaril (Glimepirid), which is a prolonged effect preparation and has significant benefits compared to other preparations of this group. Diabeton MR and Glibenese-retard are preparations of the prolonged effect. It should be noted, that patients suffering diabetes mellitus often reveal, so-called, secondary resistance towards sulphonylureas, this is caused by the elevation of residual insulin secretion. Sulphonilureas have significant side effects: dyspeptic disorder, allergic reactions, bone marrow function oppression, toxic effect on liver and kidney, hypoglycemia. There are also used biguanids, such as metformin (Glucophage, Siofor e.t.c.), Glitazones or insulin sensitizers: Actose and Avandia and alpha-glycosidase inhibitors: Acarbose and Meglitol. These oral preparations increase tissue sensitivity to insulin and exert positive normalising effect on carbohydrate metabolism. Nevertheless their application can be restricted due to low effectiveness or side effects (Balabolkin M. I., Diabetology.—M.: Meditzina, 2000.—672 p.: Register of Pharmaceutical Substances of Russia. Edition 10.—RLS-2003, Moscow.—2003.—1438 pp.)

There is known a decapeptide insulin fragment (Patent of the Russian Federation No.2078769 <<Peptide fragment, possessing biological insulin similar activity>>, International Classification of Inventions (ICI) A61 K 38/28, 1997), revealing biological activity similar to that of insulin.

There are known the peptide p277 (epitop of the human heat shock protein (hsp 60) analogues (Patent of the Russian Federation No.2159250 <<Peptide p277 analogues and pharmacological substances on its basis for treatment and diagnostics of diabetes mellitus>>, International Classification of Inventions (ICI) A61 K 39/00,38/00, 2000).

Nevertheless, the biological activity, described in the above patents, reveals in the insulin-like effect of these peptides and can be used in order to invent peptide substances for type 1 diabetes mellitus treatment.

There are known small insulin-potentiating peptides, described in the patent (EP No. 1268518 <<Insulin potentiating peptides>>, International Classification of Inventions (ICI) C07K5/10; A61K38/07; A61K38/08, 2001), which was taken as a prototype for the pharmaceutical preparation and method of prevention or/and treatment for diabetes mellitus. These small peptides can serve as peptide pharmaceutical agents, which can be used in treatment for diabetes mellitus.

It should be noted that the proposed peptide compound is a tetrapeptide, which has no structural analogues.

The proposed invention is designed to obtain a new biologically active compound of peptide nature regulating the glucose level in the patients suffering type 2 and type 1 diabetes mellitus.

The present invention describes a new tetrapeptide lysyl-glutamyl-aspartyl-tryptophane amid of the general formula Lys-Glu-Asp-Trp-$NH_2$ of sequence 1 [SEQ ID NO:1].

The tetrapeptide is obtained by a classical method of peptide synthesis in a solution (Yakubke Kh.—D., Eshkeit Kh. Amino acids, peptides, proteins: Translated from German.—Mir, Moscow.—1985.—456 pp.).

The present invention describes tetrapeptide lysyl-glutamyl-aspartyl-tryptophane amid of the general formula Lys-Glu-Asp-Trp-$NH_2$ of sequence 1 [SEQ ID NO:1] revealing biological activity, and namely, regulating glucose level.

The regulatory effect of Lys-Glu-Asp-Trp-$NH_2$ [SEQ ID NO:1] tetrapeptide on the blood glucose level has been revealed experimentally in alloxan diabetes. It is believed that alloxan diabetes is associated with the injury of the β-cells of the pancreas and is accompanied by the pronounced hyperglycaemia due to insulin deficiency and glyconeogenesis activation.

The tetrapeptide Lys-Glu-Asp-Trp-$NH_2$ [SEQ ID NO:1] was experimentally proved to be non-toxic.

The pharmaceutical substance of the present invention contains as its active peptide agent an effective amount of tetrapeptide lysyl-glutamyl-aspartyl-tryptophane amid of the general formula Lys-Glu-Asp-Trp-$NH_2$ of the sequence 1 [SEQ ID NO:1] and regulates glucose level in case of diabetes mellitus.

The notion "pharmaceutical substance" under this application implies the use of any drug form containing the effective amount of the tetrapeptide of the general formula Lys-Glu-Asp-Trp-$NH_2$ [SEQ ID NO:1] which can find its preventive and/or therapeutic employment in medicine as a substance regulating blood glucose level in case of diabetes mellitus.

The notion "therapeutically effective amount" under this application implies the use of such an amount of the active peptide agent, which, in compliance with the quantitative indices of its activity and toxicity, as well as with respect to the special knowledge available, shall be effective in this drug form.

To obtain pharmaceutical compositions meeting the invention, the proposed tetrapeptide is blended as an active ingredient with a pharmaceutical carrier in accordance with the methods of compounding accepted in pharmaceutics.

The carrier may have various forms depending on the drug form of the substance desirable for introduction into a body, for example parenteral or oral administration.

To produce drug compositions of desirable dosed form for oral administration there can be used all known pharmaceutical components.

The carrier for parenteral administration usually includes sterile water, though there could be employed other ingredients instrumental for stability or maintaining sterility.

The proposed invention presupposes that the pharmaceutical substance should be preferably prescribed for the parenteral or oral administration.

The proposed invention also refers to the method of prevention and/or treatment of diabetes mellitus, which consists in administering to the patient of the pharmacological substance, containing as an active peptide agent an effective amount of tetrapeptide Lys-Glu-Asp-Trp-NH$_2$ [SEQ ID NO:1] in doses of 0.1-30 μg/kg of the body weight at least once a day during the period necessary to obtain therapeutic effect.

The method of prophylaxis and/or treatment of diabetes mellitus consists in preventive or treatment parenteral or oral administering to the patient of the pharmacological substance.

The proposed tetrapeptide is active when introduced in doses of 0.1-30 μg/kg of the body weight, though lower/higher doses are admissible depending on the character and severity of the treated pathologic process.

Technical result of the proposed invention is a regulation of the glucose level due to the insulin secretion increase and increase of tissue sensitivity to insulin.

The possibility of obtaining an objective technical result of the invention application is affirmed by the reliable experimental and clinical data obtained by the methods established in this field of science.

The invention is illustrated by the tables.

Table 1 demonstrates the effect of tetrapeptide Lys-Glu-Asp-Trp-NH$_2$ [SEQ ID NO:1] on blood glucose level of the rats with alloxan diabetes (treatment).

Table 2 demonstrates the effect of tetrapeptide Lys-Glu-Asp-Trp-NH$_2$ [SEQ ID NO:1] on blood glucose level of the rats with alloxan diabetes (prevention and treatment).

Table 3 demonstrates the effect of tetrapeptide Lys-Glu-Asp-Trp-NH$_2$ [SEQ ID NO:1] in different doses on blood glucose level of the rats with alloxan diabetes.

Table 4 demonstrates the effect of tetrapeptide Lys-Glu-Asp-Trp-NH$_2$ [SEQ ID NO:1] on insulin level in blood of the rats with alloxan diabetes.

Table 5 demonstrates the results of the glucose tolerance test in the rats with alloxan diabetes (the 44$^{th}$ day after the tetrapeptide Lys-Glu-Asp-Trp-NH$_2$ [SEQ ID NO:1] course completion).

Table 6 demonstrates insulin effect on blood glucose level of the rats with alloxan diabetes (the 28$^{th}$ day after the tetrapeptide Lys-Glu-Asp-Trp-NH$_2$ [SEQ ID NO:1] course completion).

Table 7 represents distribution of the patients with diabetes mellitus during the study.

Table 8 demonstrates the effectiveness of the tetrapeptide Lys-Glu-Asp-Trp-NH$_2$ [SEQ ID NO:1] parenteral administration to patients, suffering type 1 and type 2 diabetes mellitus, who were treated with insulin.

The proposed invention is illustrated by the example of the tetrapeptide Lys-Glu-Asp-Trp-NH$_2$ [SEQ ID NO:1] synthesis (Example 1), by the examples of the tetrapeptide Lys-Glu-Asp-Trp-NH$_2$ [SEQ ID NO:1] biological activity (Examples 2, 3, 4, 5, 6, 7), and by the example of the results of tetrapeptide Lys-Glu-Asp-Trp-NH$_2$ [SEQ ID NO:1] clinical application, which demonstrates its pharmacological properties and confirms the possibility to achieve prophylactic or/and treatment effect (Example 8).

EXAMPLE 1.

Synthesis of Lys-Glu-Asp-Trp-NH$_2$ [SEQ ID NO:1] tetrapeptide

1. Product name: lysyl-glutamyl-aspartyl-tryptophane amid [SEQ ID NO:1]
2. Structural formula:

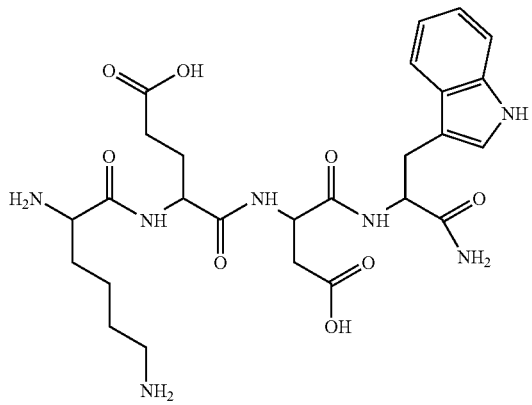

H-Lys-Glu-Asp-Trp-NH$_2$ [SEQ ID NO: 1]

3. Molecular formula without ion pair: $C_{26}H_{37}N_7O_8$.
4. Molecular weight without ion pair: 575,62.
5. Ion pair: none.
6. Appearance: white amorphous powder without smell.
7. Method of synthesis: the peptide is obtained by a classical method of synthesis in a solution by the following scheme:

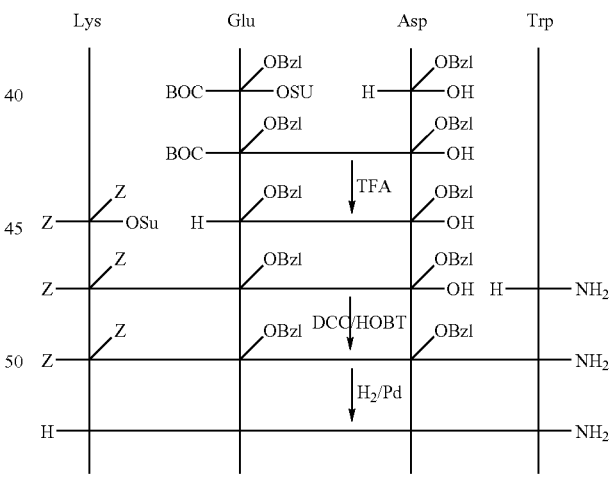

[SEQ ID NO: 1]

Z—benzyloxycarbonyl group;
BOC—tert.butyloxycarbonyl group;
OSu—N-oxysuccinimide ester;
OBzl—benzyl ester;
DCC—N,N'-dicyclohexylcarbondiimide;
HOBT—N-oxybenzotriazol.

N,N'-dimethylformamide was used as a solvent. When adding aspartic acid, the defence of α-COOH group was applied by salification with triethylamine. BOC-protecting group was removed with trifluoracetic acid (TFA) solution and Z-protecting groups—with catalytic hydrogenation. The product was extracted and purified by the method of preparative chromatography on a normal phase column (silicagel).

Properties of the finished product:
amino acid analysis

| Lys | Glu | Asp | Trp |
|------|------|------|------|
| 0.95 | 1.00 | 1.06 | 0.90 | peptide content 97.48% (by HPLC, 220 nm);
thin layer chromatography (TLC)—individual, $R_f$=0.64 (plate PTSX-P-V-UV Sorbfil, silicagel STX-1VE 8-12 µm acetonitrile:water 3:1);
moisture content: 7%;
pH of 0.01%-solution: 4.05;
UV-spectrum: the highest point at 280 nm—trypthophane indole ring
specific rotary power: $[\alpha]_D^{23}$: −26.53° (c=1.0; $H_2O$), "Polamat A", Carl Zeiss Jena Example of Synthesis 1. BOC-Glu(OBzl)-Asp(OBzl)-OH(I), N-tert.butyloxycarbonyl-(γ-benzyl)glutamyl-(β-benzyl)aspartate 4.34 g (0.0100 mol) of N-oxysuccinimide ester of N-tert-.butyloxycarbonyl-(γ-benzyl)glutamic acid (BOC-Glu(OBzl)-OSu) is dissolved in 20 ml of dimethylformamide and added 1.72 ml (0.0125 mol) of triethylamine and 2.80 g (0.0125 mol) of β-benzyl aspartate. The mixture is stirred for 24 hours at room temperature. Afterwards the product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water. The product is dried over anhydrous $Na_2SO_4$. Ethyl acetate is filtered and removed in vacuo at 40° C., the residue is dried in vacuo over $P_2O_5$. 5.68 g (≈100%) of oil is obtained. $R_f$=0.42 (benzene-acetone 2:1, Sorbfil plates, Silicagel—8-12 µm, development by UV and chlorine/benzidine).

2. TFA.H-Glu(OBzl)-Asp(OBzl)-OH (II), (γ-benzyl)glutamyl-(β-benzyl)aspartate trifluoracetate 5.68 g (≈0.01 mol) of N-tert.butyloxycarbonyl-(γ-benzyl)glutamyl-(β-benzyl)aspartate (I) is dissolved in 20 ml of dichlormethan-trifluoracetic acid mixture (3:1). Two hours later the solvent is removed in vacuo at 40° C. The removal is repeated with an addition of another portion of dichlormethan (2×10 ml). The residue is dried in vacuo over NaOH. 5.80 g (≈100%) of oil is obtained. $R_f$=0.63 (n-butanol-pyridine-acetic acid-water, 15:10:3:12).

3. Z-Lys(Z)-Glu(OBzl)-Asp(OBzl)-OH (III), N,N$^\epsilon$-dibenzyloxycarbonyllysyl-(γ-benzyl)glutamyl-(βbenzyl)aspartate 5.65 g (0.01 mol) of (γ-benzyl)glutamyl-(β-benzyl)aspartate trifluoracetate (II) is dissolved in 10 ml of dimethylformamide, added 2.80 ml (0.02 mol) of triethylamine and 6.64 g (0.013 mol) of N-oxysuccinimide ester of N,N$^\epsilon$-dibenzyloxycarbonyllysine. The reacting mixture is stirred for 24 hours at room temperature.

The product is precipitated with 0.5 n sulphuric acid solution (150 ml), extracted by ethyl acetate (3×30 ml), washed in 0.5 n sulphuric acid solution (2×20 ml), water, 5% sodium bicarbonate solution (1×20 ml), water, 0.5 n sulphuric acid solution (2×20 ml), water and dried over anhydrous sodium sulphate. Ethyl acetate is filtered and removed in vacuo at 40° C. The residue is recrystallised in the ethyl acetate/hexane system. The product is filtered and dried in vacuo over $P_2O_5$. The yield is 6.04 g (72%). The temperature of melting ($T_{ml}$) is 142° C. $R_f$=0.60 (benzene-acetone, 1:1).

4. Z-Lys(Z)-Glu(OBzl)-Asp(OBzl)-Trp-NH$_2$ [SEQ ID NO: 2] (IV), 1024.15 N,N$^\epsilon$-dibenzyloxycarbonyllysyl-(γ-benzyl)glutamyl-(β-benzyl)aspartyl-tryptophan amid 1.8 g (7.2 µmol) of tryptophan amid hydrochloride (HCl H-Trp-NH$_2$) is suspended in 15 ml of tetrahydrofuran and added 1.0 ml (7.2 mmol) of triethylamine while stirring. In 5 minutes 4.0 g (4.8 mmol) of N,N$^\epsilon$-dibenzyloxycarbonyllysyl-(γ-benzyl)glutamyl-(β-benzyl)aspartate (III) and 0.8 g (5.8 mmol) of N-oxybenzotriazol are added. The mixture is cooled down to 0° C. Afterwards, 1.2 g (5.8 mmol) of N,N'-dicyclohexylcarbodiimide solution cooled down to 0° C. is added in 5 ml of tetrahydrofuran. The mixture is stirred at this temperature for 2 hours and left to blend for a night at room temperature. The reaction mixture is poured into the ice-cold water (150 ml), the residue is grinded and filtered out. The residue is suspended in ethyl acetate (200 ml) and the generated gel is washed consecutively 1 N $H_2SO$ in water (2×100 ml), 5% $NaHCO_3$ (2×100 ml), 1N $H_2SO_4$ (2×100 ml) in water (2×100 ml), in saturate NaCl solution. The solvent is removed in vacuo and the product is twice crystallised in the isopropyl alcohol. The yield is 4.9 g (95%), $R_f$=0.67 (benzene-acetone, 2:1).

5. H-Lys-Glu-Asp-Trp-NH$_2$ [SEQ ID NO:1] (V), lysyl-glutamyl-aspartyl-triptophane amid, 575.62

4.7 g of N,N$^\epsilon$-dicarbobenzyloxylysyl-(γ-benzyl)glutamyl-(β-benzyl)aspartyl-triptophane amid (IV) [SEQ ID NO: 2] is hydrogenated in the methanol/water (5:1) system over Pd/C catalyst. Completeness of the deblocking reaction is monitored by TLC method in the benzene/acetone (2:1) and acetonitrile/water (1:3) systems. At the reaction completion the catalyst is filtered out, the filtrate is removed in vacuo and the residue is recrystallised in the water/methanol system. The product is dried in vacuo over KOH. The yield is 2.6 g (90%). $R_f$=0.64 (acetonitrile/water, 1:1).

For purification, 2.6 mg of the product is dissolved in 5 ml acetonitrile-water mixture (1:3) and put on the column 21×4.5 cm with "Sigma" silicagel, 230-400 mesh (40-63µ). Eluation was carried out by the acetonitrile-water (1:3) system. There was obtained 1 g chromatographically homogenous substance.

6. Analysis of the Finished Product

Peptide content is defined by HPLC on Nucleosil column C18 4.6×250 mm. A: 0.1% TFA; B: MeCN; grad. B 0→30% in 30 min. The flow speed equals 1 ml/min. Detection by 220 nm, scanning—by 190-600 nm, the sample volume is 20 µl. Peptide content—97.48%.

Amino acid analysis is carried out on AAA "T-339" tester, Prague.

| Lys | Glu | Asp | Trp |
|------|------|------|------|
| 0.95 | 1.00 | 1.06 | 0.90 |

TLC: individual, $R_f$=0.64 (acetonitrile/water, 3:1, Sorbfil plates, 8-12 μm Silicagel, developing in chlorine/benzidine and UV).

Moisture content: 7% (gravimetrically, according to the mass loss by drying,—20 mg at 100° C.).

pH of 0.01% solution: 4.05 (potentiometrically)

Specific rotary power: $[\alpha]_D^{23}$: −26.53° (c=1.0 H$_2$O), "Polamat A", Carl Zeiγ Jena.

UV-spectrum: peak by 280 nm—indole ring of tryptophane, "Beckman DU 650 ", 0.001% water solution.

EXAMPLE 2

Effect of tetrapeptide Lys-Glu-Asp-Trp-NH$_2$ [SEQ ID NO:1] on the Course of Alloxan Diabetes in Rats (Treatment Variant)

The study was conducted on 21 white mongrel male rats with average body weight 375±35 g. After estimation of glucose concentration in the blood all the animals were divided at random into 2 groups. Then all the animals were exposed to single intravenous administration 1 ml of alloxan solution ("Spofa") in dose 35 mg/kg. In 15 days control animals were administered once a day intraperitoneally with 0.3 ml 0.9% NaCl solution, rats of the main group were administered with Lys-Glu-Asp-Trp-NH$_2$ [SEQ ID NO:1] in dose 3 μg (in 0.3 ml of 0.9% NaCl solution) per rat during 11 days.

Table 1 shows the results of the study which reveal that Lys-Glu-Asp-Trp-NH$_2$ [SEQ ID NO:1] tetrapeptide administration contributed to the reliable decrease of the blood glucose level in the animals throughout the whole study by 38.4% (30-47.7%). Lys-Glu-Asp-Trp-NH$_2$ [SEQ ID NO:1] tetrapeptide-related glucose level decrease correlated with the lethality decrease in animals of the main group. So in the animals of the control group by the end of the investigation (84 days after alloxan administration) lethality was 70%, while in the rats which were administered with Lys-Glu-Asp-Trp-NH$_2$ [SEQ ID NO:1] tetrapeptide—36.4%. Thus the Lys-Glu-Asp-Trp-NH$_2$ [SEQ ID NO:1] tetrapeptide administration enabled two-fold lethality decrease in alloxan diabetes animals.

EXAMPLE 3

Effect of Lys-Glu-Asp-Trp-NH$_2$ [SEQ ID NO:1] on the Course of Alloxan Diabetes in Rats (Prophylaxis and Treatment Variant)

The experiment was carried out on 15 white mongrel male rats with the average body weight 375±35 g. The animals were divided randomly into 2 groups. Control animals were administered once a day intravenously with 0.3 ml of 0.9% NaCl solution, while the main group animals were administered with Lys-Glu-Asp-Trp-NH$_2$ [SEQ ID NO:1] tetrapeptide in dose of 3 μg (in 0.3 ml of 0.9% NaCl solution) per rat during 7 days. After that all the animals were subject to single intravenous administration of 1 ml of alloxan solution ("Spofa") in dose 35 mg/kg. Lys-Glu-Asp-Trp-NH$_2$ [SEQ ID NO:1] tetrapeptide had been administered during 3 days following alloxan administration. After that control rats were subject to the second Lys-Glu-Asp-Trp-NH$_2$ [SEQ ID NO:1] tetrapeptide course from 18 day till day 28 (total 11 days) in the same dose.

The results of the study are shown in table 2. First of all, it should be mentioned that Lys-Glu-Asp-Trp-NH$_2$ [ID NO:1] tetrapeptide administration to healthy animals did not lead to the decrease of blood glucose level. Control animals during the whole experimental period after alloxan administration revealed diabetes mellitus development accompanied by the increased glucose concentration in the blood 1.9-4.9 times as compared to initial level. The rats subjected to one course of Lys-Glu-Asp-Trp-NH$_2$ [SEQ ID NO:1] tetrapeptide revealed a decrease of blood glucose level by 22-30% as compared to the controls. After the second course of Lys-Glu-Asp-Trp-NH$_2$ [SEQ ID NO:1] tetrapeptide these animals revealed a complete normalisation of the blood glucose level in all experimental periods (the $28^{th}$, $33^{rd}$, $40^{th}$ day), while in the animals of the control group the blood glucose level was correspondently 2; 4.2; 3.8 fold increased.

It should be noted, that only 2 rats out of 8 treated with Lys-Glu-Asp-Trp-NH$_2$ [SEQ ID NO:1] tetrapeptide reported severe form of diabetes mellitus, while in the control group there were 5 rats out of 7, thus, in the control group this index was 2.9 fold higher.

On completion of the study (the $40^{th}$ day after alloxan administration), there survived 57.1% of the control animals and 75% of the animals treated with Lys-Glu-Asp-Trp-NH$_2$ [SEQ ID NO:1] tetrapeptide.

The results of the study show that Lys-Glu-Asp-Trp-NH$_2$ [SEQ ID NO:1] tetrapeptide contributes to the normalisation of the glucose level in alloxan diabetes rats, which is accompanied by the decrease of lethality.

EXAMPLE 4

Effect of Lys-Glu-Asp-Trp-NH$_2$ [SEQ ID NO:] tetrapeptide in Different Doses on the Course of Alloxan Diabetes in Rats The study was performed on 23 white mongrel male rats weighing on average 375=35 g. All the animals were subject to single intravenous administration of 1 ml of alloxan ("Spofa") solution in dose of 35 μg/kg.

Then the animals were divided at random into 3 groups. Control animals were intraperitoneally administered with 0.3 ml of 0.9% NaCl solution once a day. Rats of the second and third group were administered with tetrapeptide Lys-Glu-Asp-Trp-NH$_2$ [SEQ ID NO:1] in dose of 1 μg (in 0.1 ml of 0.9% NaCl solution) and 10 μg (in 1.0 ml of 0.9% NaCl solution) per rat during 7 days.

Table 3 demonstrates the results of this experiment. The administration of tetrapeptide Lys-Glu-Asp-Trp-NH$_2$ [SEQ ID NO:1] to rats in dose of 1 μg contributed to the pronounced increase in the blood glucose level on the $1^{st}$ and the $4^{th}$ days after completion of the tetrapeptide course by 17.3 and 12.3% correspondingly as compared to the controls. Tetrapeptide Lys-Glu-Asp-Trp-NH$_2$ [SEQ ID NO:1] administration to rats in dose of 10 μg led to even more pronounced decrease of glucose level by 30; 23.8; 26; 12.7% on day 1, 4, 7, 17 correspondingly. These data show that the increase of tetrapeptide Lys-Glu-Asp-Trp-NH$_2$ [SEQ ID NO:1] dose pronouncedly effects on blood glucose level of animals.

EXAMPLE 5

Effect of tetrapeptide Lys-Glu-Asp-Trp-NH$_2$ [SEQ ID NO:] on Blood Glucose Level of Alloxan Diabetes Rats The experiment was held on 18 white mongrel rats weighing an average 375±35 g. After the estimation of the blood glucose level all the animals were divided at random into 2 groups. Then all the animals were subjected to single intravenous injection with 1 ml of alloxan solution ("Spofa") in dose of 35 mg/kg. 15 days later control animals were daily intraperitoneally administered with 0.3 ml of 0.9% NaCl solution, rats of the main group—with tetrapeptide Lys-Glu-Asp-Trp-NH$_2$ [SEQ ID NO:1] in dose of 3 µg (in 0.3 ml of 0.9% NaCl) per rat during 11 days.

The results of the experiment are represented in table 4, which demonstrates that on day 15 after alloxan administration the animals reported diabetes mellitus. In the rats administered with tetrapeptide Lys-Glu-Asp-Trp-NH$_2$ [SEQ ID NO:1] insulin content in the blood during 8 days after the substance had been administered was 3.9 fold higher than in rats of the control group. All the following estimations conducted during the experiment revealed some amount of insulin in the blood of the rats (13-18%), though there was no insulin at all in the blood of the control animals. On completion of the experiment (on the 70$^{th}$ day after alloxan administration) 62.5% of the control animals were alive, in the animals administered with tetrapeptide Lys-Glu-Asp-Trp-NH$_2$ [SEQ ID NO:1] 70% were alive.

The analysis of the results of this experiment showed that administration of tetrapeptide Lys-Glu-Asp-Trp-NH$_2$ [SEQ ID NO:1] to animals with alloxan diabetes contributes to the maintenance of the insulin blood level, which can result from the partial restoration of the insulin producing cell structure and function.

EXAMPLE 6

Effect of tetrapeptide Lys-Glu-Asp-Trp-NH$_2$ [SEQ ID NO:1] on Indices of Sugar Curve in Alloxan Diabetes Rats (Treatment Variant)

The study was conducted on 13 male rats, enrolled in the previous tests (treatment variants—44 days after completion of tetrapeptide Lys-Glu-Asp-Trp-NH$_2$ [SEQ ID NO:1] administration). 7 healthy rats with the same body weight constituted a separate group. All the animals were administered intravenously with 1 ml of 2% glucose solution, after that glucose concentration in their blood was estimated.

Table 5 demonstrates the results of the trial, which reveal that in healthy rats after glucose administration its concentration was 5 min later—203.9%, 30 min—156.3%, 60 min —124.6%, 120 min—114.5% compared to the initial level (100%). In control animals the same index was correspondingly 129.8; 127.5; 123.5; 121.1%. These data point at the strong suppression of the pancreas function after alloxan lesion. The same index in rats, which were administered with Lys-Glu-Asp-Trp-NH$_2$ [SEQ ID NO:1] tetrapeptide was 142.9; 97.3; 95.6; 77.9%. The results of this trial reveal that Lys-Glu-Asp-Trp-NH$_2$ [SEQ ID NO:1] tetrapeptide can stimulate pancreas function in rats, suffering alloxan diabetes.

EXAMPLE 7

Insulin Effect on Blood Glucose Level in Alloxan Diabetes Rats after Lys-Glu-Asp-Trp-NH$_2$ [SEQ ID NO:1] tetrapeptide administration The study was conducted on 13 male rats, enrolled in the previous trial (treatment variant—28 days after completion of Lys-Glu-Asp-Trp-NH$_2$ [SEQ ID NO:1] tetrapeptide administration). 8 healthy rats of the similar body weight constituted a separate group. All the animals were administered intravenously with insulin (0.3 units) and glucose concentration in their blood was estimated hereafter.

The results of the study are shown in table 6. Healthy animals revealed a strong physiological decrease in glucose level, while in control animals (suffering alloxan diabetes) this index was 2.8 times lower. Alloxan diabetes animals treated with Lys-Glu-Asp-Trp-NH$_2$ [SEQ ID NO:1] tetrapeptide, revealed a reliable nearly two-fold decrease of the glucose level after insulin administration as compared to the control group. These data suggests Lys-Glu-Asp-Trp-NH$_2$ [SEQ ID NO:1] tetrapeptide ability to a great extent maintain tissue sensibility to insulin.

The properties of Lys-Glu-Asp-Trp-NH$_2$ [SEQ ID NO:1] tetrapeptide revealed during the study allow to recommend it for prophylactic and therapeutic application as a substance regulating blood glucose level in case of diabetes mellitus treatment.

The results of the clinical study of the proposed tetrapeptide shown below demonstrate its pharmacologic properties and confirm the possibility of the invention realization.

EXAMPLE 8

Efficacy of Applying Lys-Glu-Asp-Trp-NH$_2$ [SEQ ID NO:1] tetrapeptide in the Patients with Diabetes Mellitus The investigation was carried out in 36 patients aged from 16 to 83 years (7 men, 29 women). In 23 patients there was diagnosed type 1 diabetes, in 13 patients—type 2 diabetes. The disease duration varied from 1 year to 30 years. 32 patients received insulin. The majority of the patients suffering diabetes mellitus entered the hospital decompensated. Blood glucose level in these patients on an empty stomach oscillated from 9.5 to 27 µm/l; the glycosylated haemoglobin—from 7.8 to 12.7%. All the patients were prescribed a rigid diet. All the patients were stratified randomly into 2 groups, with respect to age, sex, duration and stage of the disease (Table 7). Alongside with standard method of treatment 16 patients were prescribed Lys-Glu-Asp-Trp-NH$_2$ [SEQ ID NO:1] tetrapeptide in dose of 10 µg (in 1 ml of 0.9% NaCl solution) intramuscularly once a day for 10 days. 4 patients suffering type 2 diabetes mellitus were prescribed together with standard treatment course Lys-Glu-Asp-Trp-NH$_2$ [SEQ ID NO:1] tetrapeptide in dose of 100 µg (1 tablet) twice a day before meals during 10 days. Patients of the control group were administered with 1 ml of 0.9% of NaCl solution as a placebo following the same scheme.

The results of the study of the Lys-Glu-Asp-Trp-NH$_2$ [SEQ ID NO:1] tetrapeptide efficacy are shown in Table 8. In 8 patients (out of 16 treated insulin) Lys-Glu-Asp-Trp-NH$_2$ [SEQ ID NO:1] tetrapeptide course resulted in reduction of the insulin daily dose by 8 units on average, this allowed to achieve the compensation.

For 6 patients the dose of insulin remained unchanged and there was registered a compensation. Only for two patients in order to achieve compensation the insulin dose was increased: the 1$^{st}$ patient—by 4 units; the 2$^{nd}$ patient—by 14 units. At the same time in control group (16 insulin administered patients) only for 2 patients the dose of insulin remained unchanged, for 14 patients the dose of insulin was increased by 4-8 units in order to achieve compensation.

In patients of the main group suffering type 2 diabetes mellitus (1 patient) and type 1 diabetes mellitus (3 patients), who received Lys-Glu-Asp-Trp-NH$_2$ [SEQ ID NO:1] tetrapeptide in tablets daily, the dose of insulin was reduced by 25 units and in patients, who were treated with oral antidiabetic medicine, there was achieved a full compensation and the dose of preparations was reduced practically two-fold.

Thus, the application of Lys-Glu-Asp-Trp-NH$_2$ [SEQ ID NO:1] tetrapeptide in patients suffering diabetes mellitus contributed to the increase of tissues sensitivity towards insulin and to some extent to pancreas function restoration. It should be noticed that there was registered rather high effectiveness of Lys-Glu-Asp-Trp-NH$_2$ [SEQ ID NO:1] tetrapeptide, which was evidenced by the decrease of insulin dose in 50% of patients of the main group, while none of the patients in control group revealed this result.

In confirmation of the said above we adduce 3 short extracts from the case histories.

Extract from the Case History No. 1.

Patient K., 69 years old, group 2 invalid. The patient has been suffering diabetes mellitus for 17 years. Since 1986 she has received anti-diabetic medicine in tablets, since 1996 these drugs were substituted with insulin. The examination of the patient revealed late diabetic complications.

Diagnosis: type 2 diabetes mellitus, secondary resistance towards insulin, diabetic retinopathy, polyneuropathy, diabetic nephropathy, symptomatic hypertension.

On the admission for treatment: blood glucose level—10 μmol/l, two hours after meals—14 μmol/l. Blood clinical analysis—normal, proteinuria—up to 0.66 g/l, ECG—hypertrophy of the left heart ventricle. Daily dose of insulin—82 units.

Therapy: diet, vitamins of B group, berlition, parenteral form of the pharmaceutical composition, containing Lys-Glu-Asp-Trp-NH$_2$ [SEQ ID NO:1] tetrapeptide, 10 μg intramuscularly during 10 days.

Discharge from the hospital on the 18th day: blood glucose level on an empty stomach—5.9 μmol/l. Daily dose of insulin—56 units (decrease by 26 units as compared to the initial level). There is a pronounced improvement in coagulogram indices.

Extract from the Case History No. 2

Patient M., 40 years, group 2 invalid. He has been suffering diabetes mellitus for 13 years and right from the onset of the disease treated with insulin.

Diagnosis: type 1 diabetes mellitus, average stage, diabetic retinopathy, polyneuropathy, encephalopathy.

On the admission for treatment: Blood glucose level on an empty stomach—17.8 μmol/l. Clinical blood and urine analysis—normal. Daily dose of insulin—40 units.

Therapy: diet, vitamins of B group, parenteral form of the pharmaceutical composition, containing Lys-Glu-Asp-Trp-NH$_2$ [SEQ ID NO:1] tetrapeptide, 10 μg intramuscularly during 10 days.

Discharge from the hospital on the 15th day: blood glucose level on an empty stomach—3.4 μmol/l. Daily norm of insulin—32 units (decrease by 8 units as compared to the initial level).

Extract from the Case History No. 3.

Patient L., 83 years old. She has been suffering diabetes mellitus for 25 years, was treated with different antidiabetic pills. Follows strict diet, recent state of the patient is satisfactory.

Diagnosis: Type 2 diabetes mellitus, diabetic retinopathy.

On admission for treatment: blood glucose level on an empty stomach—11 μmol/l. Clinical blood and urine analysis—normal. Takes 2 tab. of diabeton daily. As the patient had revealed resistance towards pilled antidiabetic preparations she was recommended to take insulin. But the patient declined to be treated with insulin, that was why she was prescribed oral form of pharmaceutical composition, containing Lys-Glu-Asp-Trp-NH$_2$ [SEQ ID NO:1] tetrapeptide, 100 μg (1 tab) twice a day before meals during 10 days together with the intake of 2 diabeton tablets. On the second day glucose level on an empty stomach was 6 μmol/l. Then the dose of diabeton was reduced two-fold. After the completion of the treatment course with Lys-Glu-Asp-Trp-NH$_2$ [SEQ ID NO:1] tetrapeptide the blood glucose level remained within the norm. Present state of the patient is satisfactory.

TABLE 1

| Animal group | Initial level | 15 days after alloxan administration | 8 days since the onset of Lys-Glu-Asp-Trp-NH$_2$ [SEQ ID NO: 1] tetrapeptide administration | Upon completion of peptide Lys-Glu-Asp-Trp-NH$_2$ [SEQ ID NO: 1] administration (days) | | | | | |
|---|---|---|---|---|---|---|---|---|---|
| | | | | 1 | 9 | 18 | 28 | 44 | 58 |
| Control (NaCl) | 84.0 ± 5.7 | 345.0 ± 15.4 | 360.0 ± 12.3 | 342.5 ± 17.3 | 351.4 ± 11.2 | 368.3 ± 8.1 | 375.7 ± 12.8 | 347.2 ± 12.8 | 332.1 ± 13.7 |
| n | 10 | 10 | 9 | 8 | 7 | 6 | 5 | 5 | 3 |
| Tetrapeptide Lys-Glu-Asp-Trp-NH$_2$ [SEQ ID NO: 1] | 81.1 ± 3.8 | 333.6 ± 12.4 | 254.5 ± 16.2 | 222.5 ± 10.3* | 183.9 ± 10.5* | 236.7 ± 10.3* | 221.5 ± 11.2* | 210.8 ± 9.3* | 198.9 ± 11.5* |
| n | 11 | 11 | 11 | 10 | 9 | 9 | 8 | 8 | 7 |

*P < 0.001 as compared to the control.

TABLE 2

| | Glucose Concentration in blood (mg %) | | | | | | | |
|---|---|---|---|---|---|---|---|---|
| | | 7 days from the onset of Lys-Glu-Asp-Trp-NH$_2$ [SEQ ID NO: 1] tetrapeptide administration | After alloxan administration (days) | | | | | |
| | | | | | 18 | 28 2$^{nd}$ course of Lys-Glu-Asp-Trp-NH$_2$ [SEQ ID NO: 1] tetrapeptide administration | | |
| Animal group | Initial level | (1 course) | 5 | 14 | | (from 18$^{th}$ till 28$^{th}$ day) | 33 | 40 |
| Control (NaCl) | 82.7 ± 0.9 | 96.4 ± 1.0 | 351.7 ± 19.4* | 333.7 ± 55.8* | 345.6 ± 57.8* | 156.4 ± 26.4* | 383.0 ± 89.3* | 405.0 ± 89.8* |
| n | 7 | 7 | 7 | 6 | 5 | 5 | 4 | 4 |
| Tetrapeptide Lys-Glu-Asp-Trp-NH$_2$ [SEQ ID NO: 1] | 76.8 ± 1.1 | 94.0 ± 0.8 | 247.3 ± 17.2*# | 261.5 ± 39.5*# | 159.0 ± 32.6*# | 77.3 ± 1.3# | 90.7 ± 5.2# | 107.7 ± 6.4# |
| n | 8 | 8 | 8 | 8 | 6 | 6 | 6 | 6 |

*P < 0.001 as compared to the control;
P < 0.02 as compared to the control.

TABLE 3

| | Glucose Concentration in blood (mg %) | | | | | | | |
|---|---|---|---|---|---|---|---|---|
| | | After alloxan administration (days) | | After Lys-Glu-Asp-Trp-NH$_2$ [SEQ ID NO: 1] tetrapeptide administration (days) | | | | |
| Animal group | Initial level | 7 | 14 | 1 | 4 | 7 | 14 | 21 |
| Control (NaCl) | 78.6 ± 4.2 | 276.4 ± 0.9 | 272.1 ± 9.8 | 275.7 ± 9.7 | 278.6 ± 9.8 | 277.9 ± 11.1 | 275.0 ± 10.5 | 285.0 ± 12.9 |
| n | 7 | 7 | 7 | 7 | 7 | 7 | 6 | 6 |
| Tetrapeptide Lys-Glu-Asp-Trp-NH$_2$ [SEQ ID NO: 1] (1 mkg) | 80.6 ± 2.8 | 245.6 ± 12.3 | 261.7 ± 12.3 | 228.3 ± 10.7* | 244.4 ± 12.2* | 269.4 ± 8.6 | 268.8 ± 12.4 | 272.5 ± 9.9 |
| n | 9 | 9 | 9 | 9 | 8 | 8 | 8 | 8 |
| Tetrapeptide Lys-Glu-Asp-Trp-NH$_2$ [SEQ ID NO: 1] (10 mkg) | 83.9 ± 3.4 | 247.2 ± 14.0 | 252.2 ± 7.9 | 193.3 ± 6.7* | 212.2 ± 7.3* | 205.6 ± 8.4* | 240.0 ± 7.9* | 248.3 ± 13.5 |
| n | 7 | 7 | 7 | 7 | 7 | 7 | 6 | 6 |

*P < 0.05 as compared to the control.

TABLE 4

Insulin content in blood (mkIU/ml)

| Animal group | Initial level | 15 days after alloxan administration | 8 days since the onset of Lys-Glu-Asp-Trp-NH$_2$ [SEQ ID NO: 1] tetrapeptide administration | After the completion of tetrapeptide Lys-Glu-Asp-Trp-NH$_2$ [SEQ ID NO: 1] administration (days) | | | | |
|---|---|---|---|---|---|---|---|---|
| | | | | 1 | 9 | 18 | 28 | 44 |
| Control (NaCl) | 24.3 ± 2.1 | 2.0 ± 0.7 | 0.8 ± 0.25 | 0 | 0 | 0 | 0 | 0 |
| n | 8 | 8 | 8 | | | | | |
| Tetrapeptide Lys-Glu-Asp-Trp-NH$_2$ [SEQ ID NO: 1] | 23.8 ± 2.8 | 1.5 ± 0.4 | 3.1 ± 1.1* | 3.6 ± 0.7# | 3.2 ± 0.5# | 4.3 ± 0.5# | 4.1 ± 0.6# | 3.9 ± 1.1# |
| n | 10 | 10 | 10 | 8 | 7 | 7 | 7 | 7 |

*P < 0.05 as compared to the control
P < 0.001 as compared to the control.

TABLE 5

| | | Time after glucose administration (min) | | | |
|---|---|---|---|---|---|
| Animal group | Initial level | 5 | 30 | 60 | 120 |
| Healthy | 84.5 ± 4.2 | 172.3 ± 8.1 | 132.1 ± 9.1 | 105.3 ± 6.2 | 96.8 ± 5.3 |
| n | 7 | 7 | 7 | 7 | 7 |
| Control (NaCl) | 347.2 ± 12.8* | 450.5 ± 15.2* | 442.7 ± 14.3* | 428.9 ± 14.1 | 420.5 ± 16.5 |
| n | 5 | 5 | 5 | 5 | 5 |
| Tetrapeptide Lys-Glu-Asp-Trp-NH$_2$ [SEQ ID NO: 1] | 210.8 ± 9.3# | 301.2 ± 10.5# | 205.1 ± 11.8# | 201.5 ± 13.2# | 164.2 ± 12.8# |
| n | 8 | 8 | 8 | 8 | 8 |

*P < 0.001 as compared to healthy animals;
P < 0.05 as compared to the control.

TABLE 6

| | Glucose concentration in blood (mg %) | | Decrease in glucose content with respect to initial level (%) |
|---|---|---|---|
| Animal group | Initial level | 30 minutes after insulin administration | |
| Healthy | 83.5 ± 3.2 | 29.4 ± 2.2 | 64.8 |
| n | 8 | 8 | |
| Control (NaCl) | 375.7 ± 11.2* | 287.8 ± 12.5* | 23.4 |
| n | 5 | 5 | |
| Tetrapeptide Lys-Glu-Asp-Trp-NH$_2$ [SEQ ID NO: 1] | 221.5 ± 11.2# | 123.6 ± 8.3# | 44.2 |
| n | 8 | 8 | |

*P < 0.001 as compared to healthy animals;
P < 0.05 as compared to the control.

TABLE 7

| | Group of patients | |
|---|---|---|
| Index | Control (placebo) | Main (tetrapeptide Lys-Glu-Asp-Trp-NH$_2$ [SEQ ID NO: 1]) |
| Number of patients | 16 | 20 |
| Men | 3 | 4 |
| Women | 13 | 16 |
| Number of patients with type 1 diabetes mellitus | 11 | 12 |
| Number of patients with type 2 diabetes mellitus | 5 | 8 |

TABLE 8

| | Group of patients | |
|---|---|---|
| Index | Control (placebo) | Main (tetrapeptide Lys-Glu-Asp-Trp-NH$_2$ [SEQ ID NO: 1]) |
| Number of patients | 16 | 16 |
| Decreased insulin dose necessary to achieve compensation | 0 | 8 |
| The same insulin dose necessary to achieve compensation | 2 | 6 |
| Increased insulin dose necessary to achieve compensation | 14 | 2 |

The invention claimed is:

1. Tetrapeptide Lys-Glu-Asp-Trp-$NH_2$[SEQ ID NO:1].

2. A pharmaceutical composition comprising a pharmaceutically admissible carrier and tetrapeptide Lys-Glu-Asp-Trp-$NH_2$[SEQ ID NO:1].

3. The pharmaceutical composition of claim 2, which is an oral formulation.

4. The pharmaceutical composition of claim 2, which is a parenteral formulation.

5. A method of treatment of diabetes mellitus, which consists in administering to the patient an effective amount of tetrapeptide Lys-Glu-Asp-Trp-$NH_2$ [SEQ ID NO:1] at least once a day for a period necessary for attaining a therapeutic effect.

6. The method of claim 5 wherein the tetrapeptide is administered parenterally.

7. The method of claim 5 wherein the tetrapeptide is administered orally.

8. The method of claim 5 wherein the tetrapeptide is administered in doses of 0.1-30 mg/kg of the body weight.

* * * * *

```
                            SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: The tetrapeptide Lys-Glu-Asp-Trp-NH2
      regulates blood level in organism, suffering from diabetes
      mellitus, due to increasing of insulin secretion and increasing
      of tissue sensitivity of insulin.

<400> SEQUENCE: 1

Lys Glu Asp Trp
1
```